US006971392B2

(12) United States Patent
Lindahn et al.

(10) Patent No.: US 6,971,392 B2
(45) Date of Patent: Dec. 6, 2005

(54) SACRO-ILIAC MOBILIZATION TOOL

(76) Inventors: Ronald P. Lindahn, P.O. Box 24, Rabun, Gap, GA (US) 30568; Vicki Sims-Skorput, 4670 Highland Dr., Gainesville, GA (US) 30506

( * ) Notice: Subject to any disclaimer, the term of this patent is extended or adjusted under 35 U.S.C. 154(b) by 0 days.

(21) Appl. No.: 10/617,636

(22) Filed: Jul. 11, 2003

(65) Prior Publication Data

US 2005/0072436 A1 Apr. 7, 2005

Related U.S. Application Data

(60) Provisional application No. 60/395,550, filed on Jul. 12, 2002.

(51) Int. Cl.[7] .................................................. A61F 5/37

(52) U.S. Cl. ...................... 128/882; 128/845; 482/140; 482/142; 602/23; 602/32

(58) Field of Search ................................ 128/882, 845, 128/869; 602/19, 23, 24, 25, 26, 27, 28, 29, 602/32; 606/240, 241; 482/144, 145, 140, 482/142, 143

(56) References Cited

U.S. PATENT DOCUMENTS

| | | | | |
|---|---|---|---|---|
| 5,623,949 | A * | 4/1997 | Kostich | 128/845 |
| 5,669,862 | A * | 9/1997 | Sayman | 482/140 |
| 5,921,904 | A * | 7/1999 | Toups | 482/140 |
| 6,012,456 | A * | 1/2000 | Schuerch | 128/869 |
| 6,022,303 | A * | 2/2000 | Abdo | 482/140 |
| 6,126,624 | A * | 10/2000 | Frauenberger et al. | 602/23 |
| 6,234,173 | B1 * | 5/2001 | Hajianpour | 128/869 |
| 6,308,712 | B1 * | 10/2001 | Shaw | 128/869 |
| 6,422,982 | B1 * | 7/2002 | Retel | 482/144 |
| 6,468,191 | B1 * | 10/2002 | Cameron | 482/140 |

* cited by examiner

*Primary Examiner*—Fadi H. Dahbour
(74) *Attorney, Agent, or Firm*—Bruce F. Jacobs

(57) ABSTRACT

A tool for making gentle repetitive movements to the joints between a person's sacrum and ilium which allow for proper pelvic alignment when one or both have become irritated, inflamed, or malaligned, and causes significant pain. Use of the tool generates a lateral and caudal directed force on an affected ilium thereby mobilizing it back into its normal position. The tool also may be used to realign the pubic synthesis.

3 Claims, 8 Drawing Sheets

SACRO-ILIAC MOBILIZATION TOOL

This application claims benefit of Provisional 60/395,550 filed Jul. 12, 2002.

BACKGROUND OF THE INVENTION

A large percentage of lower back pain is caused by misalignment of one or both of the sacro-iliac joints. This condition tends to be chronic and results in pain in the lower back, hip and sometimes down the leg of the affected side. It can also result in problems with bladder and other pelvic disorders, uterine pain, and colon pain.

It is important that the treatment of the sacro-iliac joint be localized to avoid straining adjacent ligaments or joints. The direction and pressure applied must be specific to produce the desired release. Moreover, in order to produce long term positive results, the joint must be "reset" whenever it becomes misaligned, until the stretched ligaments and muscles return to their normal condition. Because it is impractical to revisit a physical therapist several times a day, a need has been identified for a device which willl allow an individual to 'reset' their own sacro-iliac joint as needed between visits to a medical professional. A suitable device must allow an individual to mobilize (reset) their own sacro-iliac joint by applying pressure in a vector which causes the sacrum and ilium to return to their normal position relative to the other.

Previous attempts at accomplishing this result have been as varied as the back therapy system of U.S. Pat. No. 5,217,487, the aquatic apparatus of U.S. Pat. No. 5,258,018, the sacro-iliac joint mobilization device of U.S. Pat. No. 5,626,616, and the back exercising apparatus of U.S. Pat. No. 5,971,900. None of these have been found satisfactory to enable a patient to "reset" their own sacro-iliac joint as needed between visits to a medical professional.

SUMMARY OF THE INVENTION

In accordance with the present invention, a device for localized bone mobilization in the pelvic area including a sacrum, a pair of ilia with a sacro-iliac joint disposed between the sacrum and each ilium of the human body is provided. The device comprises a base member having fixed arms oriented in a horizontal plane at an angle of approximately 45° to one another. One end of the base member serves as a handle and may be tapered for ease of holding. Affixed at the opposite end of the base member is a short rod and affixed at the intersection of the two fixed arms is a long rod extending in the same direction as the short rod. Both rods are attached substantially perpendicular to the base member.

In use this device enables an individual to generate a lateral and caudal directed force on an affected ilium thereby mobilizing it back into its normal position. The device is configured for the mobilization of one affected side of the sacro-iliac joint, and a second mirror image device configuration is needed for the opposing side of the sacro-iliac joint. Generally the device is intended for use with either the left hand or the right hand of the individual. Alternatively, to convert a device from use on the left side of the body to one useful on the right side, the rods may be disconnected from the base member and reattached to the opposite side of the base member.

After a joint has been "reset" by use of the device, a realignment of the pubic synthesis assists in maintaining proper sacroiliac joint position. The device is also configured to facilitate the alignment of the pubic synthesis by the patient. The patient places the short rod between the knees and squeezes the knees together. This produces an isometric contraction of the adductors, realigning the pubic synthesis.

BRIEF DESCRIPTION OF THE DRAWINGS

For a more complete understanding of the present invention and for further advantages thereof, reference is now made to the following Description of Preferred Embodiments taken in conjunction with the accompanying drawings in which.

DESCRIPTION OF THE PREFERRED EMBODIMENTS

Figure 1:
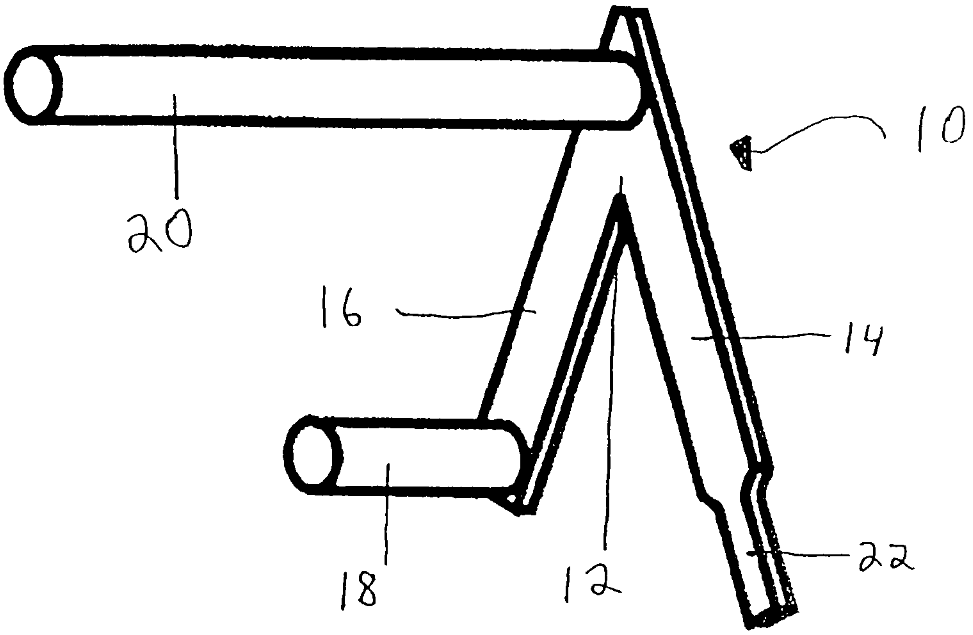
FIG. 1 is an isometric view of a device of the present invention showing a base member bent at about a 45° angle and having two rods, i.e. a long rod and a short rod, extending in the same direction therefrom.
Figure 2:
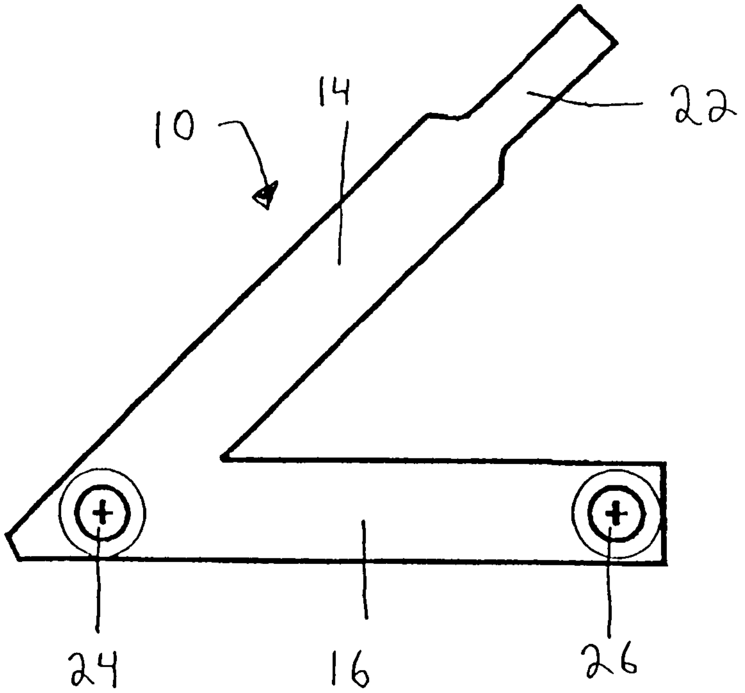
FIG. 2 is a side view of the device of FIG. 1, showing the relative relationship of the two arms of the base member and the angle therebetween.
Figure 3:
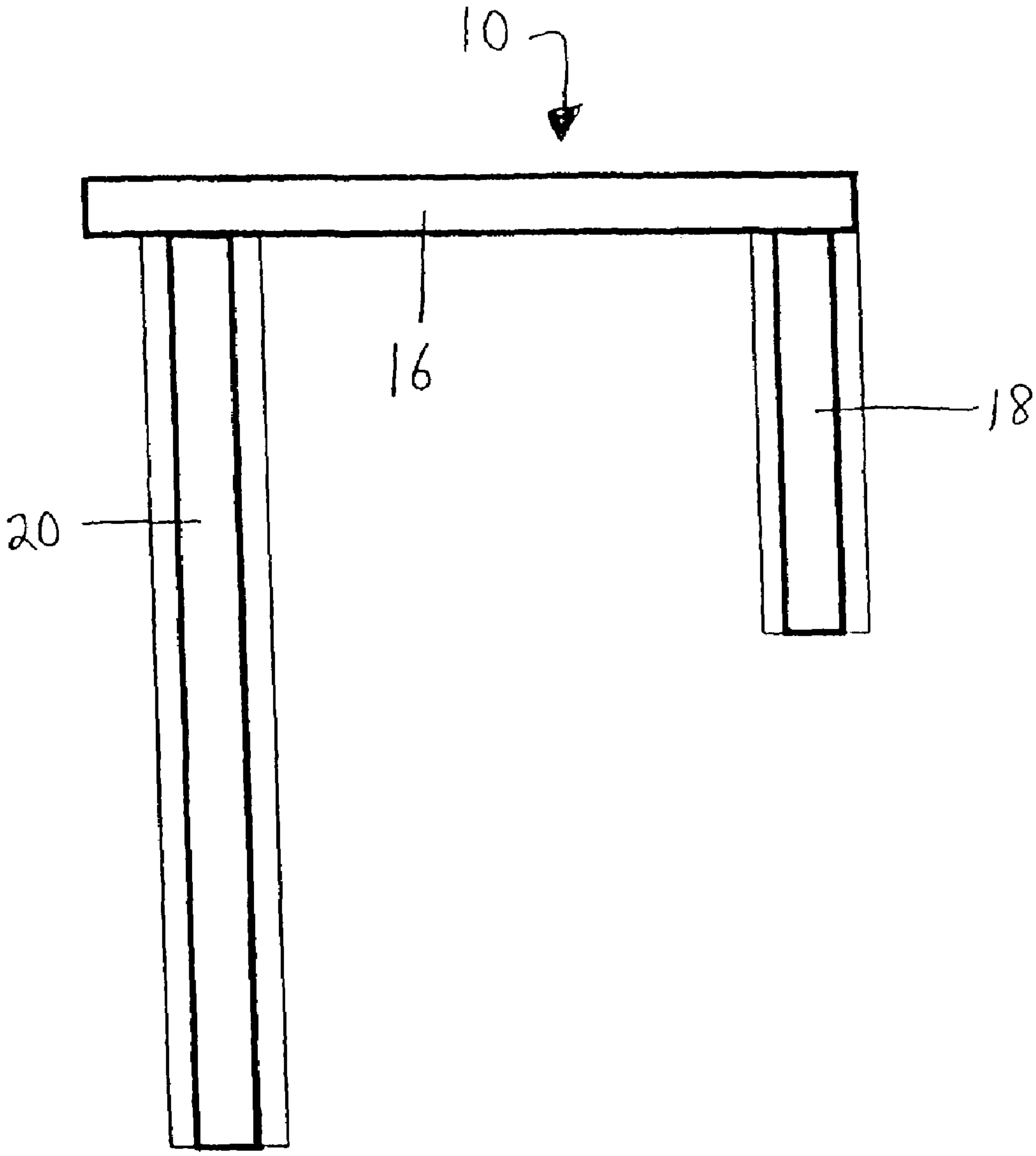
FIG. 3 is a top view of the device of FIG. 1 showing the relative position of the long and short rods.

As best seen in FIGS. 1 through 3, a mobilization tool 10 of the present invention designed for use for the right side of a body is illustrated. A suitable device for use on the left side of a body is a mirror image to mobilization tool 10 and is not shown.

As shown in FIG. 1, the mobilization tool 10 includes a base member 12 composed of a fixed arm 14 and a fixed arm 16 oriented at an angle of about 30 to 60°, preferably about 35 to 55°, and most preferably about 40 to 50°, to one another. Affixed to fixed arm 16 are two rod members. The first is a relatively short rod 18 (about 9" long) and the second is a relatively long rod 20 (about 18" long) affixed at the point where the two arms meet. Rods 18 and 20 are each attached perpendicular to the base member by any suitable means, such as screws 24, 26. The length of fixed arm 16 is about 12" long so that the short rod 18 is located about 11" from the long rod 20. Fixed arm 14 serves as a handle and is about 15" long. As shown, the fixed arm 14 is narrowed at the end away from the long rod 20 so as to form a handle area 22.

Alignment of the sacro-iliac joint with the device of the present invention is based upon passive mobilization. During use, no active muscle contraction should be facilitated. The extremity being acted upon should remain completely relaxed at all times during the mobilization process. Mobilization of the sacro-iliac joint is created by the leverage and angle facilitated by the use of the mobilization tool as it is pulled toward the patient's shoulder either by the patient or by a therapist.

Figure 4:
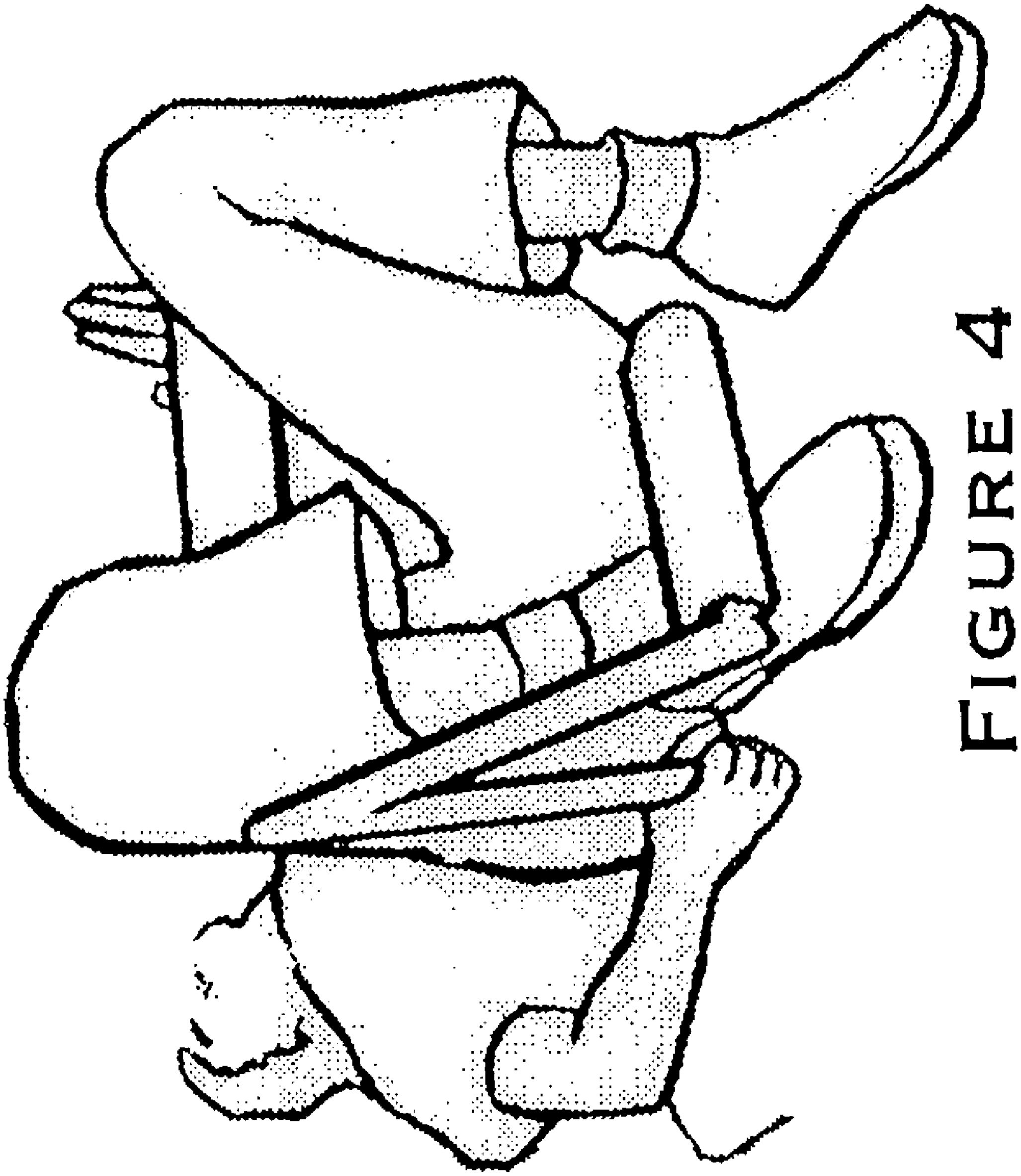
FIG. 4 shows a patient in a supine position and the device in its initial position prior to use for sacro-iliac mobilization.
Figure 5A:
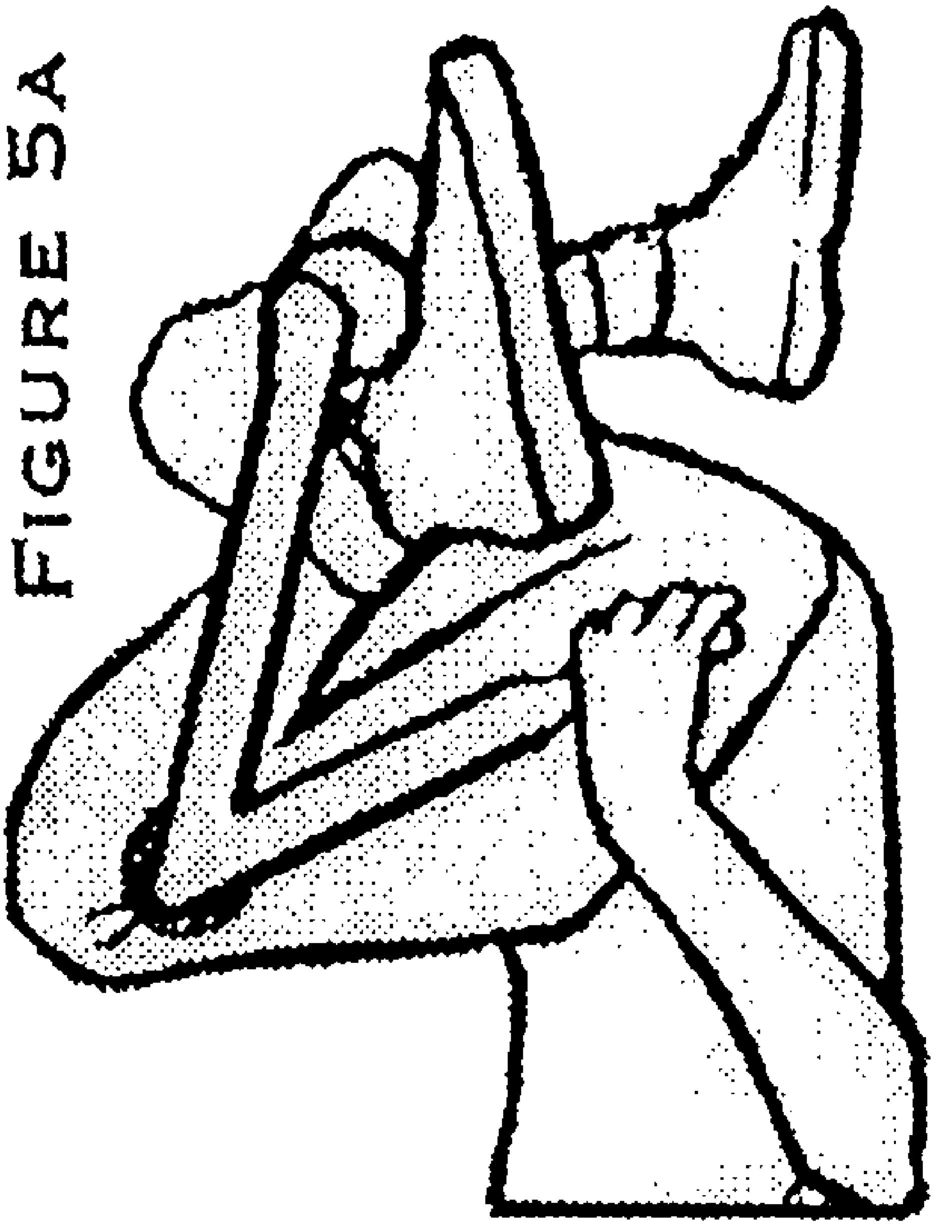
FIG. 5A is a side view and FIG. 5B is an end view showing the first motion of the device by a patient.
Figure 5B:
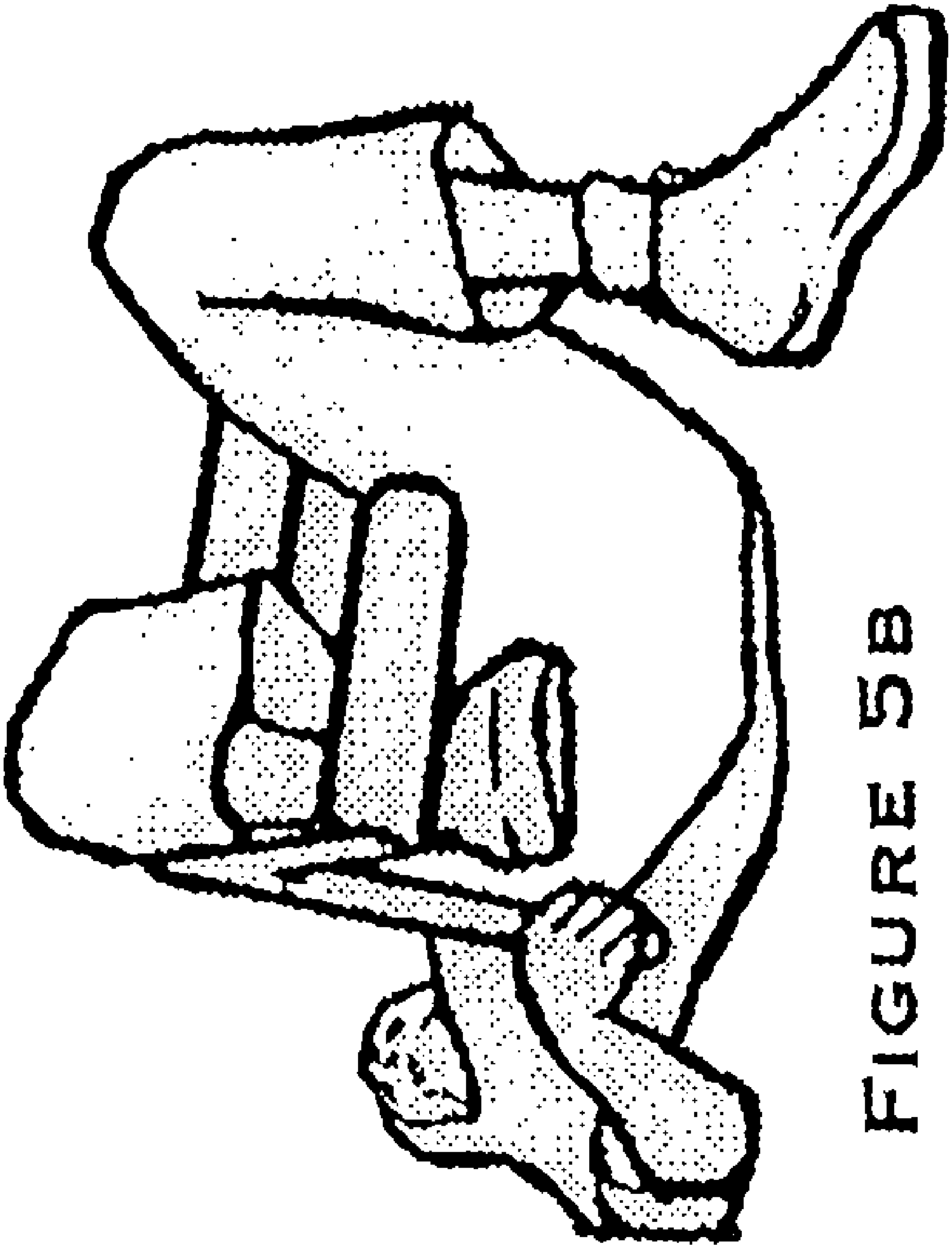
Figure 6A:
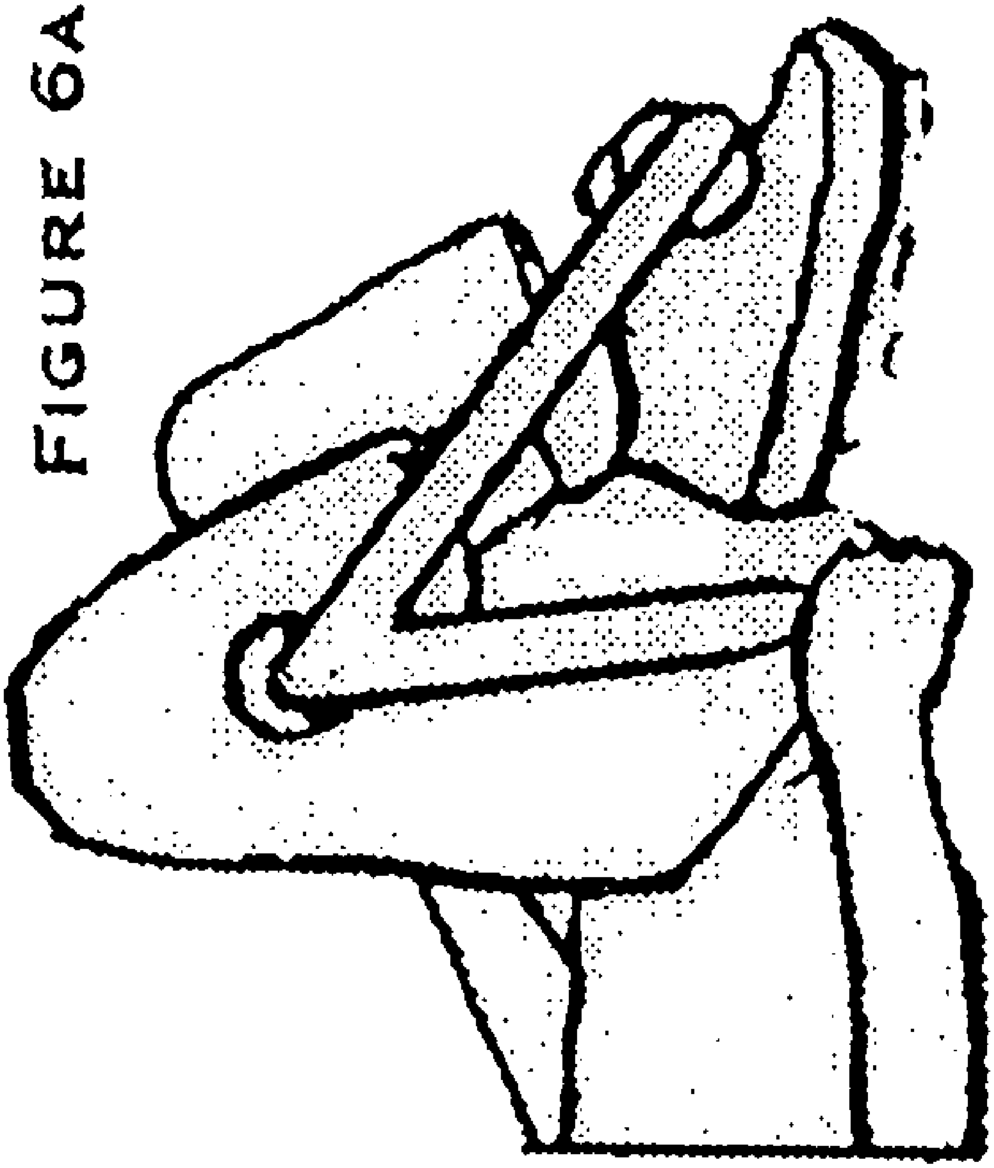
FIG. 6A is a side view and FIG. 6B is an end view showing the second motion of the device by a patient wherein mobilization of the sacroiliac joint is facilitated.

Use of the sacro-iliac mobilization tool is shown in FIGS. 4–6. FIG. 4 shows the initial positioning of the mobilization tool for use when the right side is the symptomatic side. The patient lies supine with knees bent and feet flat. The long rod 20 of tool 10 is placed beneath the right knee (the symptomatic side) and its open end is placed on top of the opposite (left) knee which remains vertical during the procedure. The patient uses his left hand to support the end of rod 20 on the upper knee of the non-symptomatic side. The short rod 18 of the tool 10 is placed across the anterior part of the lower leg on the symptomatic side.

Figure 6B:
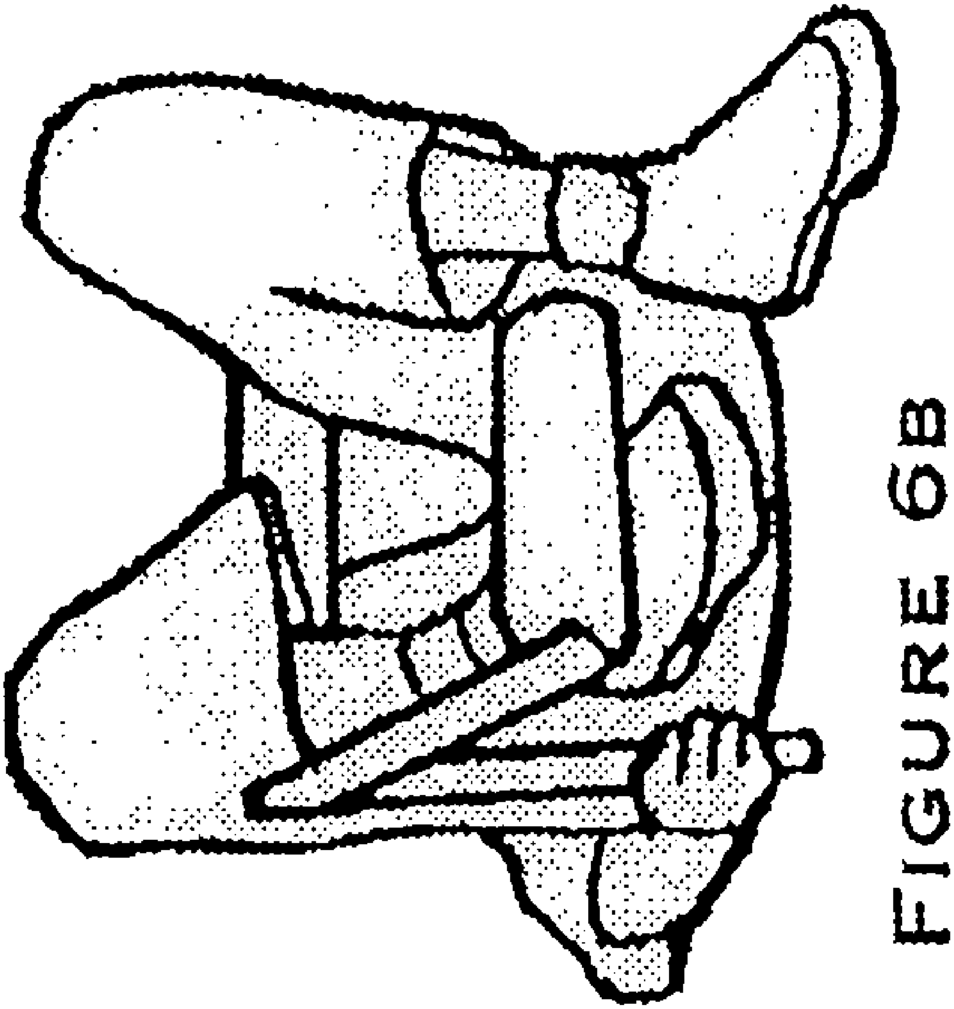

FIGS. 5A, 5B, 6A and 6B show the mobilization of the sacroiliac joint. The patient, or a therapist, grips the handle 22 of the tool 10 and pulls gently toward the patient's shoulder (see FIGS. 5A and 5B) while lifting up and out away from the body (as best seen in FIG. 6B). The gentle pulling applies force roughly perpendicular and caudal to the sacroiliac joint. The force is held for about 1 to 5 seconds, preferably about 2 seconds, and then the force is released. This procedure is repeated four or five times in a session. The sessions may be repeated multiple times in a single day as often as necessary to maintain the proper alignment.

Figure 7:
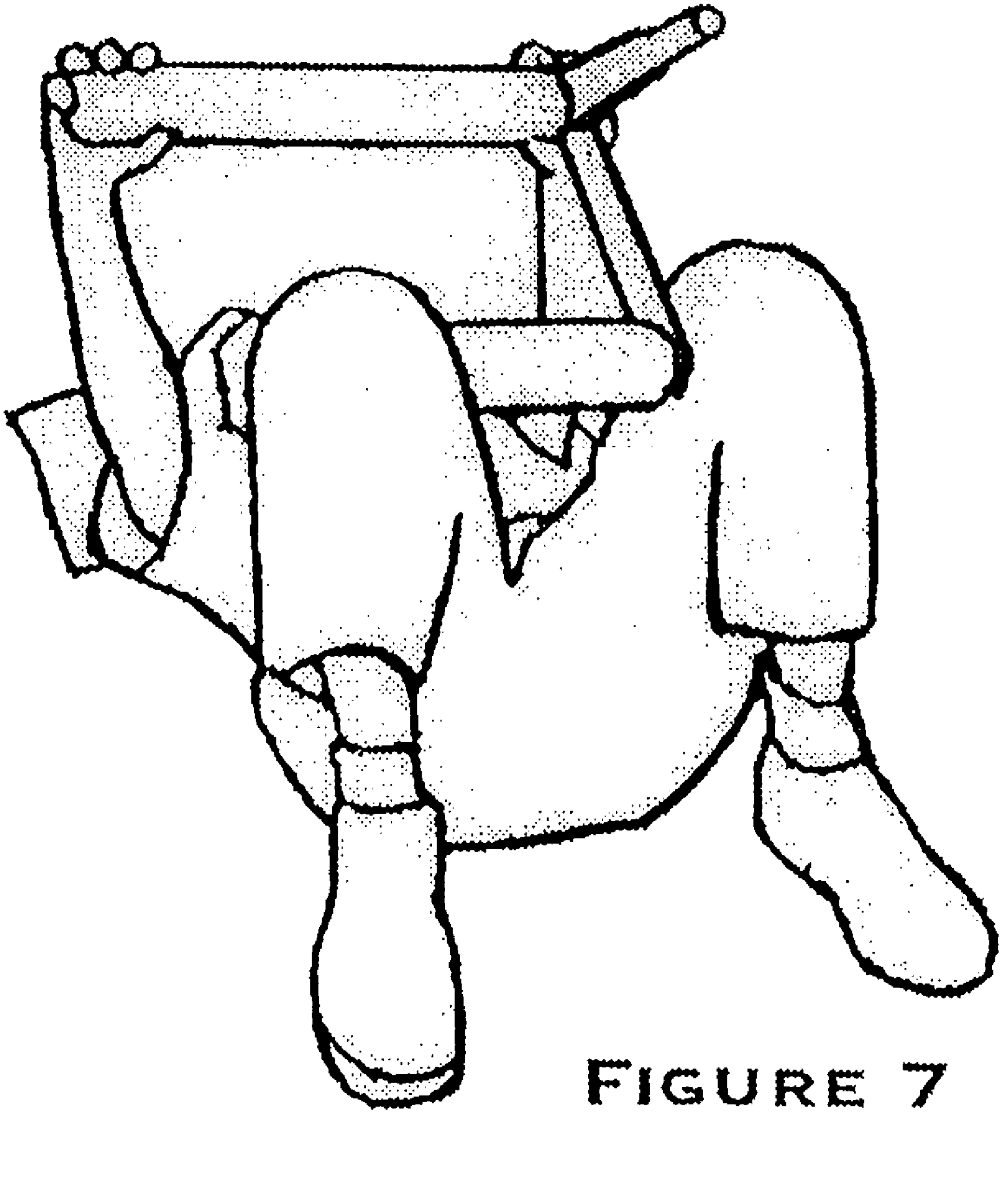
FIG. 7 shows a secondary positioning of the device and mobilization vector in order to realign the pubic synthesis.

An additional use of the sacro-iliac mobilization tool of the present invention is to cause alignment of a patient's pubic synthesis by means of a resistive mobilization technique. Alignment of the pubic synthesis is created through use of the mobilization tool as a passive resistance device. Alignment of the pubic synthesis is preferably performed following each session of mobilization of the sacro-iliac joint described above. As best seen in FIG. 7, the alignment using the mobilization tool 10 is performed by having a patient remain supine with knees bent and feet flat. The knees are then moved apart and the short rod 18 of the tool is placed between the knees. The knees are then forced together pressing against both ends of the short rod 18 and held for about five seconds. The patient then relaxes. This procedure is repeated three times.

After use of the mobilization tool for both procedures, the patient should remain at rest for several minutes, generally about six to ten minutes or more.

While the present invention has been described for self-treatment of strains of the sacro-iliac joint through localized mobilization, it may also be performed by a therapist acting upon a patient.

What is claimed is:

1. A device for localized bone manipulation in the pelvic area of the human body, the pelvis having a sacrum, a pair of ilia, and a sacro-iliac joint between the sacrum and each ilium, the device consisting essentially of:

a base member having a first arm and a second arm disposed in a horizontal plane at an angle of about 30 to 60° to each other;

a first rod member extending from an end of the first arm of the base member, perpendicular thereto about 8 to 12 inches;

a second rod member extending from the intersection of the two arms of the base member, perpendicular thereto about 15 to 20 inches in the same direction as the first rod member.

2. The device of claim 1, wherein the end of the second arm of the base member is shaped to form a handle.

3. The device of claim 1, wherein the first and second arms are disposed at an angle of about 45° to each other.

* * * * *